(12) United States Patent
Poschelk

(10) Patent No.: US 6,193,117 B1
(45) Date of Patent: Feb. 27, 2001

(54) APPARATUS AND METHOD FOR FITTING AND REMOVAL OF GLOVES

(76) Inventor: Kevin Keith Poschelk, 77 Herbert Street, Bowen Qld 4805 (AU)

( * ) Notice: Subject to any disclaimer, the term of this patent is extended or adjusted under 35 U.S.C. 154(b) by 0 days.

(21) Appl. No.: 09/269,628
(22) PCT Filed: Oct. 17, 1997
(86) PCT No.: PCT/AU97/00702
§ 371 Date: Mar. 30, 1999
§ 102(e) Date: Mar. 30, 1999
(87) PCT Pub. No.: WO98/17133
PCT Pub. Date: Apr. 30, 1998

(30) Foreign Application Priority Data

Oct. 17, 1996 (AU) .................................................. PO 3107

(51) Int. Cl.$^7$ .................................................. A47G 25/90
(52) U.S. Cl. .......................................................... 223/111
(58) Field of Search .................... 223/111, 78; 2/159, 2/160

(56) References Cited

U.S. PATENT DOCUMENTS

| | | |
|---|---|---|
| 2,741,410 * | 4/1956 | Violette .................................. 223/111 |
| 3,695,493 | 10/1972 | Karr ....................................... 223/111 |
| 4,002,276 | 1/1977 | Poncy et al. ......................... 223/111 |
| 4,069,913 * | 1/1978 | Harrigan ............................... 223/111 |
| 4,228,935 | 10/1980 | Madray ................................. 223/111 |
| 4,275,812 * | 6/1981 | Poncy et al. ......................... 223/111 |
| 4,898,309 | 2/1990 | Fischer ................................. 223/111 |
| 4,915,272 | 4/1990 | Vlock ................................... 223/111 |
| 5,058,785 | 10/1991 | Rich et al. ........................... 223/111 |
| 5,078,308 | 1/1992 | Sullivan ............................... 223/111 |

* cited by examiner

Primary Examiner—Bibhu Mohanty
(74) Attorney, Agent, or Firm—Seidel, Gonda, Lavorgna & Monaco, PC

(57) ABSTRACT

Glove fitting apparatus including cuff holding means (14) adapted to hold open the cuff opening of a glove, and adapted to release said glove after insertion of a user's hand, and support means (20) for supporting the cuff holding means. The glove may be released directly from the holding means, or alternatively, the glove may be released by way of releasing of the holding means from the support means. The retaining means may include stiffening means wherein the support means releasably holds the stiffening means and the glove supported thereby. It is also preferred that the stiffening means includes a ring assembly (14) comprising two rings which fit closely one inside the other such that when the opening of the glove is fitted over the inner ring, the outer ring may be tightly engaged about the inner ring to clamp the opening of the glove between the two rings.

17 Claims, 5 Drawing Sheets

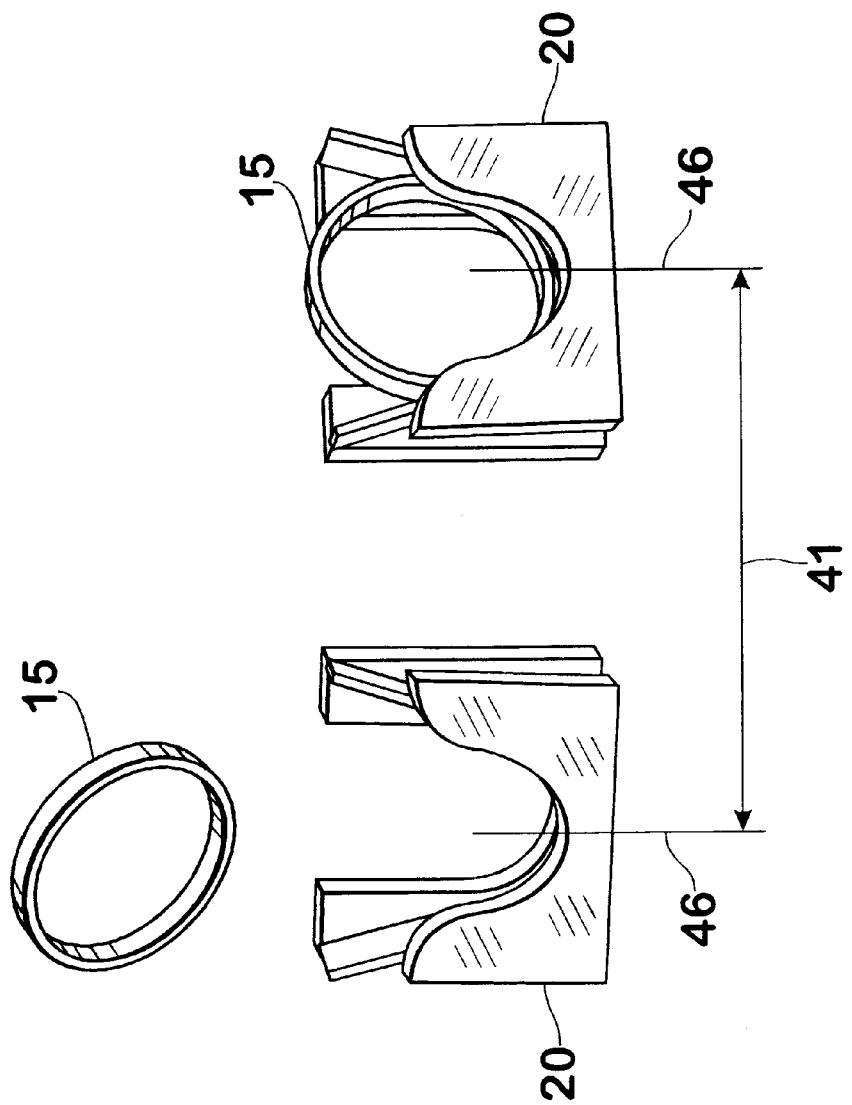

APPARATUS AND METHOD FOR FITTING AND REMOVAL OF GLOVES

Figure 2:
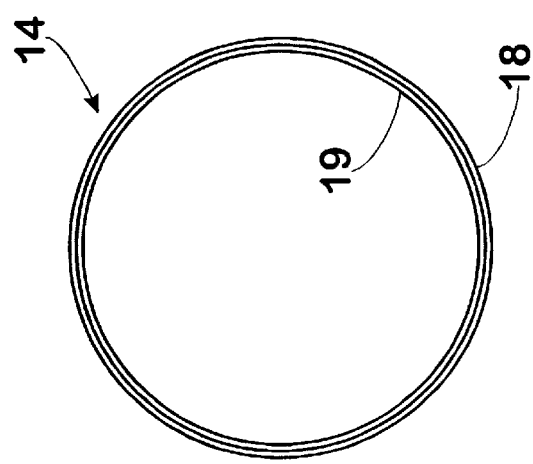

This invention relates to apparatus and methods for fitting and removal of gloves.

This invention has particular application to the fitting and removal of gloves in sterile or hygienic environments, and for illustrative purposes, reference will be made to such application. It is to be understood, however, that this invention may also be used in other applications, such as in other work environments where hands-free fitting of gloves is desirable. This invention also has application in the fitting and removal of other apparel such as mittens and such like.

In the medical industry, protective gloves are worn by surgeons and other medical practitioners to avoid contaminating a patient. Gloves may also be worn to prevent transmission of disease from the patient to the practitioner.

In sterile environments in particular, such as operating theatres and preparation rooms, surgical gloves are donned by a surgeon with the assistance of a surgeon's assistant or the like, who is already provided with gloves. In such situations, it is difficult to provide a gloved surgeon without potentially compromising the sterility of the gloves.

The present invention aims to alleviate one or more of the above disadvantages and to provide apparatus and methods for fitting of gloves which will be reliable and efficient in use.

With the foregoing in view, this invention in one aspect resides broadly in glove fitting apparatus including:

cuff holding means adapted to hold open the cuff opening of a glove, and adapted to release said glove after insertion of a user's hand, and support means for retaining said cuff holding means.

The release of the glove may be by way of releasing the glove from the holding means, or alternatively, by release of the holding means from the retaining means.

Preferably, the cuff holding means includes stiffening means and the retaining means releasably supports the stiffening means and the glove supported thereby. In one embodiment, the stiffening means includes a light stiff ring attached to the open end of the glove; and the retaining means is constituted by a rigid bracket assembly for the location of the ring. Additionally, the glove fitting apparatus may be provided in pairs, the gloves being provided in complementary left and right hand configurations.

Suitably, the ring has an internal diameter large enough for the wearer's hand to pass through unimpeded. For example, the internal diameter is the ring may be selected to be sufficient for the wearer's closed fist to pass therethrough. The ring may be moulded as an integral part of the glove, or it may be a ring assembly comprising two hoops which fit closely one inside the other such that when the opening of the glove is fitted over the inner hoop, the outer hoop may be tightly engaged about the inner hoop to clamp the opening of the glove between the two hoops. A third hoop may also be provided to enclose the two fitted hoops and provide additional clamping force to hold the glove opening in place as well as enclose the edge of the glove opening.

The ring assembly is of a configuration consistent with permitting the wearer's hand or fist to pass therethrough, such as circular, but may be oval or other shapes to conform to the usual shape of a wearer's wrist.

The retaining means is generally in the nature of opposed longitudinally spaced apart laterally extending means for retaining the opened cuff and cuff holding means. The retaining means is preferably in the form of a locating bracket adapted to releasably hold the cuff holding means.

For example, where the cuff holding means is in the form of the aforementioned ring assembly, the locating bracket assembly may consist of two thin but rigid vertical plates separated by a distance slightly wider than the width of the ring assembly. This separation of the plates is such that the ring assembly may be made to slide between them with little or no resisting force, the ring assembly being held in place by gravity.

The present invention also aims to provide apparatus and methods for removal of gloves.

In another aspect, this invention resides broadly in glove removal apparatus including:

cuff holding means adapted to hold open the cuff of a glove, and retaining means for supporting said cuff holding means for removal of a user's hand from said glove.

The glove fitting apparatus and glove removal apparatus may be incorporated into a single glove fitting and removal apparatus if required.

In another aspect, this invention resides broadly in a method of inserting a user's hand into a glove, including:

providing glove apparatus as herein before defined;

inserting the user's hand through the cuff opening means, and releasing said glove from said cuff holding means.

In another aspect, this invention resides broadly in a method of inserting a user's hand into a glove, including:

providing glove apparatus as herein before defined;

inserting the user's hand through the cuff opening means, and releasing said cuff holding means from said retaining means.

Figure 1:
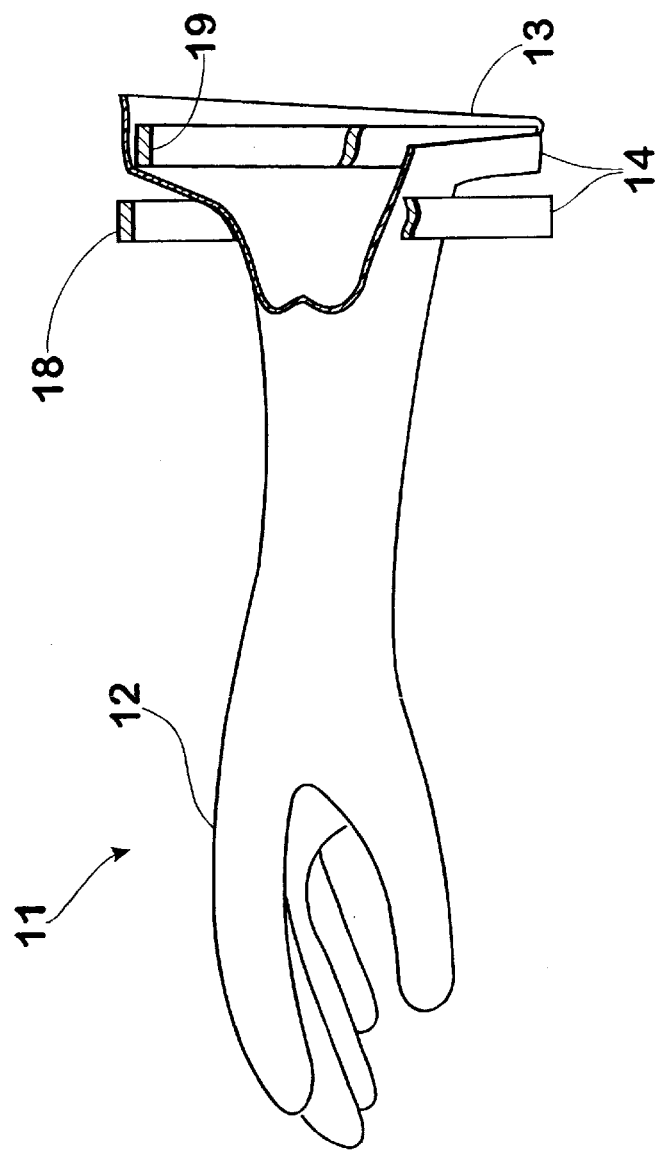
Figure 3:
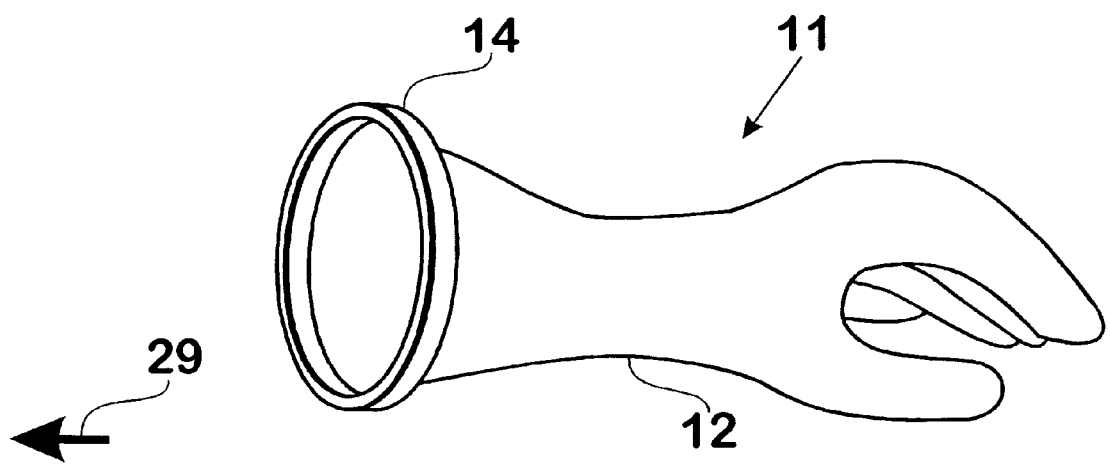
Figure 3:
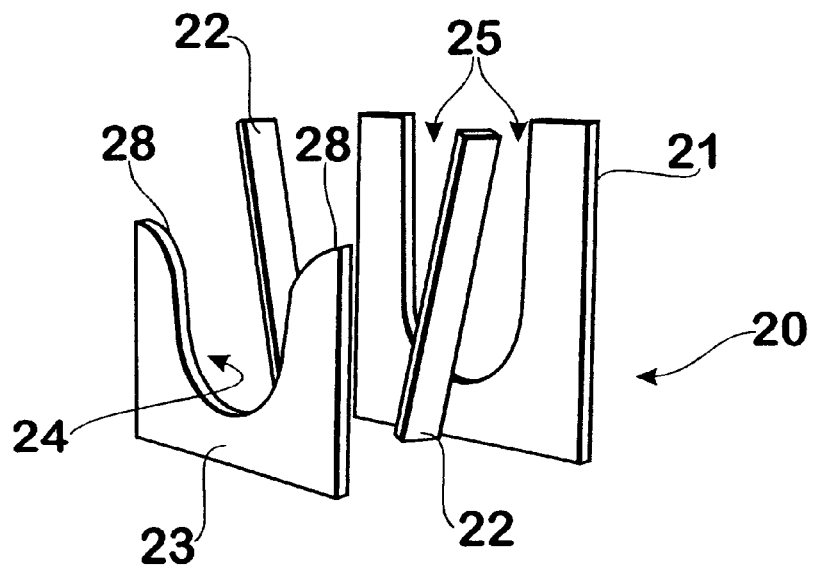

In order that this invention may be more readily understood and put into practical effect, reference will now be made to the accompanying drawings which illustrate a typical embodiment of the invention and wherein:

FIGS. 1 and 2 collectively show respectively a diagrammatic side partly exploded and cut away view and an end view of a glove assembly;

FIG. 3 is exploded view of a glove assembly and bracket assembly;

FIGS. 4 to 8 collectively show diagrammatically the steps performed using the glove assembly and bracket assembly (in sectional view) of FIGS. 1 to 3, and FIGS. 9 and 10 show the orientation of two bracket assemblies for use with complementary left-and right-handed gloves.

Referring to FIGS. 1 and 2, a glove assembly 11 includes a glove 12 having a glove opening 13 and a ring assembly 14 which comprises an inner hoop 19 and an outer hoop 18. The outer surface of the inner ring 19 is tapered to a close fit on the inner diameter of the outer hoop 18, which is also tapered. The glove opening 13 is stretched out over the outside surface of the inner hoop 19 and wedged between the inner hoop 19 and the outer hoop 18. With the material of the glove interposed between the inner and outer hoops 18 and 19 respectively, the clearance between the hoops 18 and 19 is such that the glove is clamped tightly between the hoops 18 and 19.

Referring to FIG. 3, the glove assembly 11 may be located in a bracket assembly 20, which is shown in exploded form. The bracket assembly 20 includes a back plate 21 and a front plate 23 which are separated by two guide plates 22. The front plate 23 has a front slot 24 and the back plate 21 has a back slot 25.

The front and back slots 24 and 25 include curved base portions and the respective guide plates 22 are inserted between the front plate 23 and the back plate 21 at an oblique angle to create a trapezium sectioned cavity into which the ring assembly 14 may be inserted. The insertion of the glove assembly 11 is such that the opening is towards the front plate 23, facing towards a wearer in the direction of an arrow 29.

The front plate 23 also includes respective upper curved portions 28 on each side of the front slot 24 for guiding the wrist of a user into the front slot 24 when replacing the glove assembly into the bracket assembly 20 for removing the glove 12 from the hand.

Referring to FIGS. 4 to 8, there shown are eight steps in using the glove assembly 11 and bracket assembly 20, which constitute a glove and bracket assembly 10. A user, whose hand or arm is represented at 30, may don the glove assembly 11 in the eight steps shown by way of example in FIGS. 4 to 8. It may be considered that the left hand side of FIGS. 4 to 8 represents a "dirty side", and the right hand side cf FIGS. 4 to 8 represents a "clean side".

Figure 9:
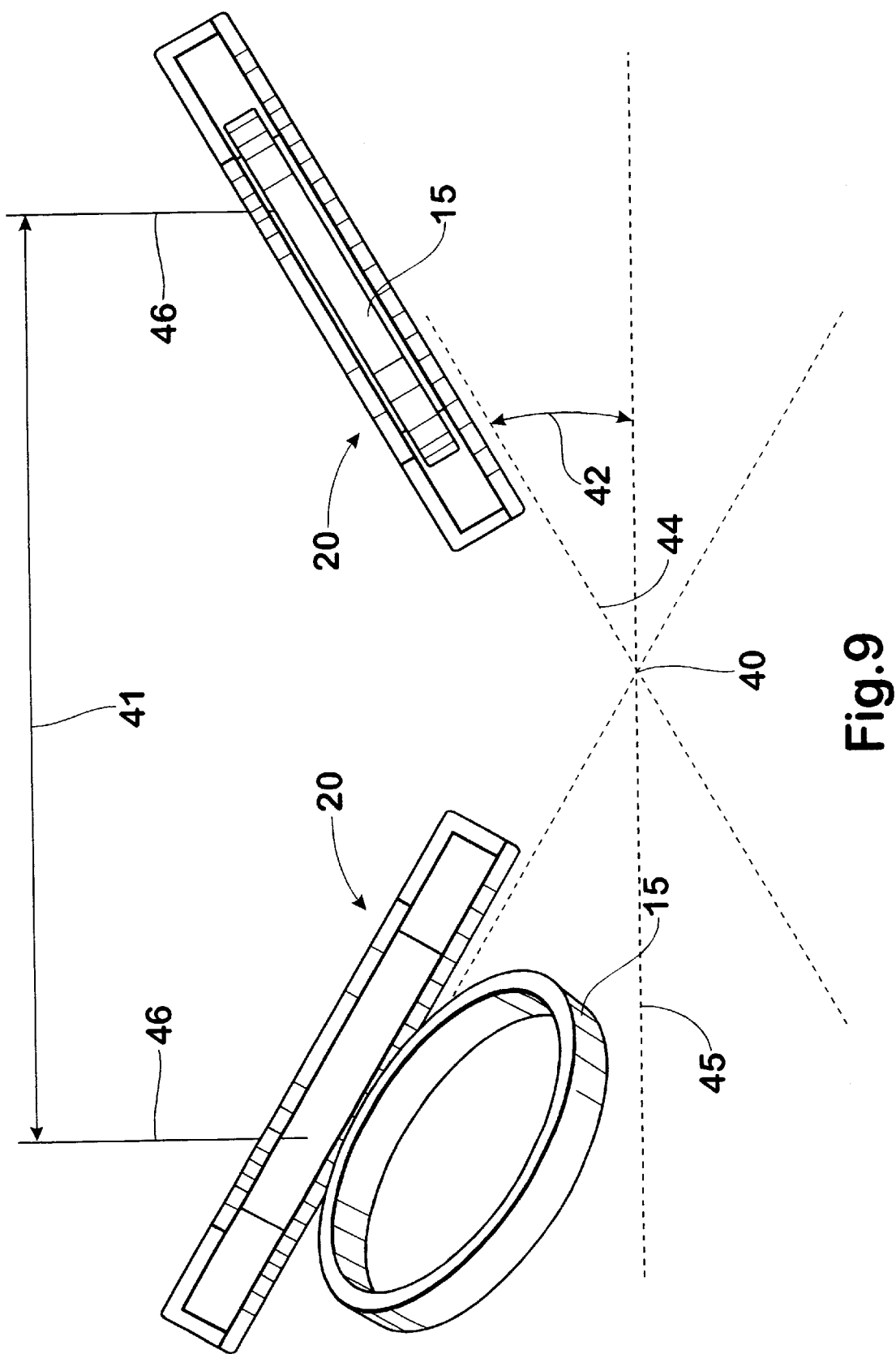

Referring to FIGS. 9 and 10, two glove and bracket assemblies 10 are provided in complementary pairs, one glove assembly 11 being for the left hand and the other glove assembly 11 being for the right hand.

The respective bracket assemblies 20 are provided in spaced apart relationship, with respective central axes 46 at a separation distance 41 of 250 mm. The respective bracket assemblies 20 are also at a preferred angle to one another in plane view, the angle being defined by the relationship of each bracket assembly 20 to a wearer's frontal plane represented by the frontal axis 45 which intersects with two respective bracket axes 44 at an axis intersection point 40. Each bracket axis 44 is at a separation angle 42 of 30°.

A glove fitting apparatus of this invention may be used to fit and/or remove gloves from a wearer as shown in particular in FIGS. 4 to 8. The slots 24 and 25 are provided with vertical sides of sufficient width to allow a wearer's fist to pass therebetween. The distance between the vertical sides of the slots 24 and 25 however is less than the internal diameter of the ring assembly 14.

The bracket assembly may be bench or wall mounted or positioned in a manner that allows adequate free access above the vertical slots. The bracket assemblies may be formed using fabricated sheet metal or plastic or cast in metal or plastic products.

Figure 4:
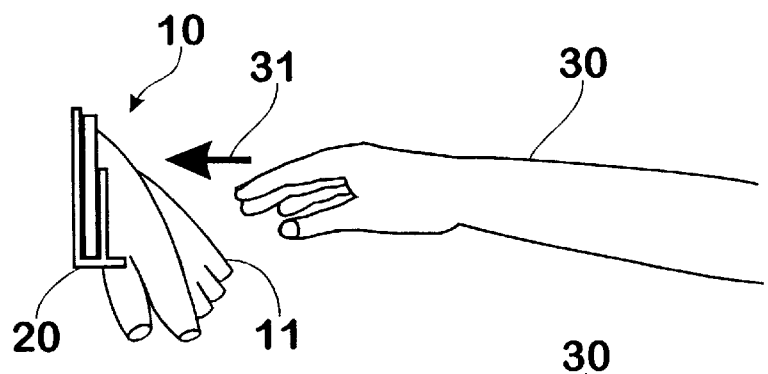
Figure 5:
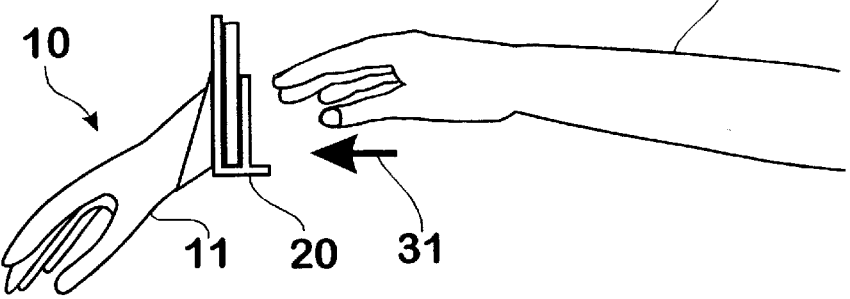
Figure 6:
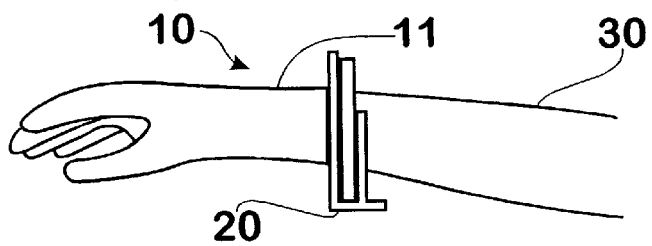
Figure 7:
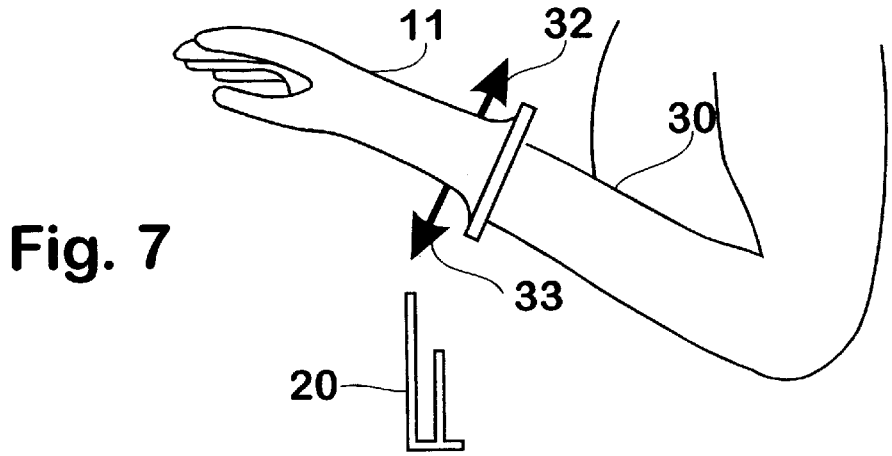
Figure 8:
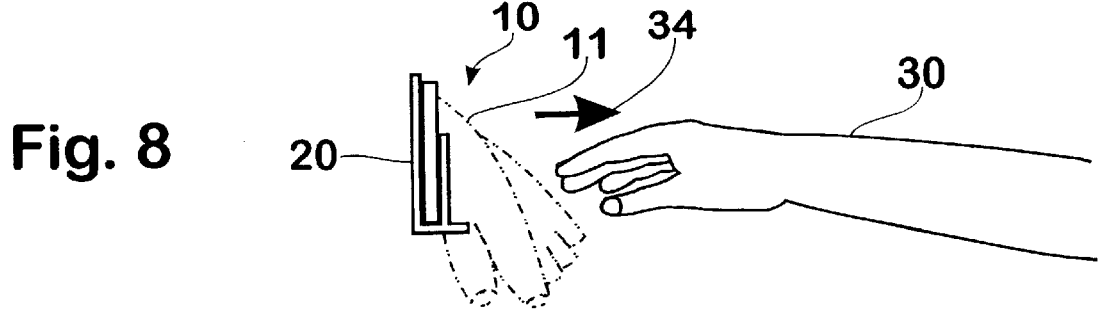

Referring to FIGS. 4 to 8, the fitting of the glove assembly 11 by a wearer may, for example, be achieved in a series of operations which are described hereinafter with reference to the steps set forth in FIGS. 4 to 8:

1) firstly placing the ring assembly 14 of the glove 12 into the bracket assembly 20;
2) if the inside surface of the glove 12 is exposed to the wearer's wrist and hand 30 being fitted with the glove 12, as shown in particular in FIG. 4, the wearer pushes the proud surface through the ring assembly 14 away from his or her body in the direction of an arrow 31, with a slightly closed hand;
3) the hand 30 then follows the inner surface of the glove 12 through the ring assembly 14 pushing the wearer's fingers into the corresponding fingers of the glove 12 being fitted;
4) once the wearer's fingers are in place and the glove 12 has been fitted, the gloved hand may be lifted to raise the glove assembly 11 up and out of the bracket assembly 20 in the direction of an arrow 32. The glove assembly 11 has been disengaged from the bracket assembly 20 allowing the wearer to utilise the glove in the usual manner.

De-gloving may also be achieved in a series of operations of the wearer, also shown as an example in FIGS. 4 to 8:

5) firstly moving the gloved hand in the direction at 90° to the plates 21 and 23 of the bracket assembly so that the ring assembly moves between the plates 21 and 23, and the wrist 30 moves between the slots 45 and 25 of these plates 21 and 23;
6) the gloved hand continues to move until the ring assembly 14 contacts the back plate 21 of the bracket assembly 20;
7) the gloved hand is then allowed to drop in the direction of an arrow 33 to permit the ring assembly 14 to fall between the front and back plates 21 and 23 of the bracket assembly 20 and is further guided into position by the two (2) rigid inclined guide plates 22 that separate the front and back plates 21 and 23.
8) Once the ring assembly 14 is held by the bracket assembly 20, such as being wedged between the guide plates, the ring assembly 14 is locked in the forward and backward direction allowing the wearer to remove his or her hand 30 from the glove 12 in the direction of an arrow 34 through the ring assembly 14 and the vertical slots 24 and 25 of the bracket assembly 20.

The glove may be left in the apparatus so that wearer can re-glove at a future time, or the glove may be removed so that another wearer can use the apparatus after placing a new glove assembly 11 into the bracket assembly 20. A mark or locating flange may be used to aid in the correct positioning of the glove on the bracket assembly to help in re-gloving.

The glove 12 may be left to hang in the apparatus so that either the inner or outer surface of the glove 12 is exposed to the atmosphere promoting faster drying. The wearer may don gloves with dry inner surfaces more rapidly.

When 2 (two) bracket assemblies 20 are used so that the wearer may simultaneously don both left hand and right hand gloves, the bracket assemblies 20 are arranged so that they are at a comfortable working height and orientation for the wearer as described in respect of FIGS. 9 and 10. When the apparatus is set up in this or a similar fashion, the wearer may use his or her left and right hands in a complementary manner to remove the gloves leaving the gloves open and ready for quicker fitting.

This apparatus and technique for the fitting and removal of gloves has multi industry use, further reducing the need for disposable gloves with both cost savings and improved environmental protection.

This invention allows the fitting and removal of gloves using only the one hand or arm that is being fitted. This single handed fitting and removal avoids the need for what is normally a two handed operation, and this reduces cross-contamination between the inside and outside surfaces of the glove.

Indeed, the glove assembly of the present invention may be used when the gloves are inside out. For donning an inside out glove, the hand of the user may grasp the inside surface to push the body of the glove through the opening in the ring assembly, pushing the fingers against the surface of the corresponding fingers of the glove until the fingers and the body of the glove are inside out.

The glove assemblies 12 of the present invention may be supplied in sterile packs with the ring assembly 14 already in place. For example, the gloves may be supplied inside out and removed from the sterile pack using a sterile utensil for placing a glove assembly 12 into a bracket assembly 20. A wearer who may have, for example, scrubbed up for performing surgical operations, is then able to don a pair of gloves without contaminating same using the glove and bracket assembly 10 of the present invention.

It will be realised that the above has been given only by way of illustrative example of the invention and that all such modifications and variations thereto as would be apparent to persons skilled in the art are deemed to fall within the broad scope and ambit of the invention as claimed in the following claims.

What is claimed is:

1. A glove fitting apparatus comprising:
   at least one stiff cuff holding ring holding a cuff of a glove open whereby a user's hand may pass through the opened cuff unimpeded;
   at least one bracket assembly into which the opened cuff may be introduced by lateral movement, said bracket assembly comprising opposed longitudinally spaced apart laterally extending means for retaining the opened cuff and cuff holding ring therebetween; and
   wherein a user's hand may be introduced to or removed from the glove by longitudinal movement through the opened cuff.

2. The glove fitting apparatus of claim 1:
   wherein said means for retaining the opened cuff captures said opened cuff and cuff holding ring for limited longitudinal movement therebetween; and
   wherein said opened cuff and cuff holding ring may be introduced to said bracket assembly by unimpeded lateral movement.

3. The glove fitting apparatus of claim 1 wherein said cuff holding ring is a lightweight circular ring about which the cuff must be stretched to an opened position.

4. The glove fitting apparatus of claim 1, wherein said cuff holding ring is sufficiently large to permit the gloved hand to pass freely therethrough whereby the gloved hand may be withdrawn through the opened cuff and the glove turned inside-out when the user's hand is withdrawn therefrom.

5. The glove fitting apparatus of claim 1, wherein said cuff holding ring is comprised of an inner hoop inside the cuff, and an outer hoop outside the cuff, said outer hoop being tightly and removably engaged about said inner hoop thereby clamping said cuff between said inner hoop and said outer hoop.

6. The glove fitting apparatus of claim 1, wherein said opposed longitudinally spaced apart laterally extending retaining means are walls formed with complementary slots therein to permit lateral entry of the cuff and cuff holding ring therebetween.

7. The glove fitting apparatus of claim 1 wherein said bracket assembly constitutes one of a pair of spaced apart bracket assemblies for capturing respective ones of a pair of gloves each fitted with a said stiff cuff holding ring holding the cuff of the respective glove open whereby a user's hands may pass through the respective opened cuffs unimpeded.

8. A method of storing gloves ready for use, comprising:
   providing a cuff holding ring, and a glove having a cuff;
   providing a bracket assembly comprising opposed longitudinally spaced apart laterally extending means for retaining the cuff holding ring;
   stretching the cuff around the cuff holding ring;
   inserting the cuff holding ring holding the cuff of the glove open into the bracket assembly in a space between the laterally extending means for retaining the cuff holding ring for retention thereby and with the glove extending to a respective side corresponding to the glove being supported in a normal or inside-out attitude.

9. A method of inserting a user's hand into a glove comprising:
   providing a cuff holding ring, and a glove having a cuff;
   providing a bracket assembly comprising opposed longitudinally spaced apart laterally extending means for retaining the cuff holding ring;
   stretching the cuff around the cuff holding ring;
   inserting the cuff holding ring holding the cuff of the glove open into the bracket assembly for retention thereby and with the glove extending to a respective side corresponding to the glove being supported in a normal or inside-out attitude;
   inserting the user's hand through the cuff of the glove; and
   laterally moving the user's hand thereby disengaging the glove and cuff holding ring from the bracket assembly.

10. A glove fitting apparatus comprising:
    a substantially rigid cuff holding ring;
    said cuff holding ring having an inner diameter, an outer diameter, and a depth transverse to the diameters;
    a bracket assembly comprising a back plate and a front plate;
    wherein said bracket assembly has a vertical axis, a bottom and a top;
    wherein said back plate is substantially parallel to said front plate, said front plate being separated from said back plate by a distance greater than the depth of the cuff holding ring;
    wherein said front plate has a front slot and said back plate has a back slot, said front slot and back slot having widths smaller that the outer diameter of the cuff holding ring; and
    wherein a space is defined between said front plate and said back plate, said space capable of receiving said cuff holding ring.

11. The glove fitting apparatus of claim 10 wherein said substantially rigid cuff holding ring comprises an inner hoop and an outer hoop, both having an inner surface and an outer surface, wherein the outer surface of the inner hoop is tapered to a close fit to the inner surface of the outer hoop, the inner surface of the outer hoop also being tapered.

12. The glove fitting apparatus of claim 10 wherein the cuff holding ring has an inner diameter large enough to allow a user's hand to pass through the ring unimpeded.

13. The glove fitting apparatus of claim 10 wherein the bracket assembly further comprises two guide plates.

14. The glove fitting apparatus of claim 13 wherein the two guide plates are substantially transversely attached to both the front plate and the back plate symmetrically about the vertical axis, said guide plates being separated by a distance slightly larger than the outer diameter of the cuff holding ring.

15. A method of storing gloves ready for use comprising:
    providing a cuff holding ring, and a glove having a cuff;
    providing a front plate and a back plate each having a slot;
    arranging the front plate and back plate such that they are substantially parallel and such that the slots on each are oriented in the same direction, thereby forming a bracket assembly;
    stretching the cuff of the glove around the cuff holding ring such that the cuff is thereby held open; and
    inserting the cuff holding ring and the cuff into a space defined between the front plate and the back plate of the bracket assembly for retention thereby and with the glove extending to a respective side corresponding to the glove being supported in a normal or inside-out attitude.

16. A method for inserting a user's hand into a glove comprising:

providing a cuff holding ring, and a glove having a cuff;

providing a front plate and a back plate each having a slot;

arranging the front plate and back plate such that they are substantially parallel and such that the slots on each are oriented in the same direction, thereby forming a bracket assembly;

stretching the cuff of the glove around the cuff holding ring such that the cuff is thereby held open;

inserting the cuff holding ring and the cuff into a space defined between the front plate and the back plate of the bracket assembly for retention thereby and with the glove extending to a respective side corresponding to the glove being supported in a normal or inside-out attitude;

inserting the user's hand through the cuff holding ring; and removing the hand and glove from the bracket assembly in a direction of motion substantially transverse to the insertion motion.

17. A method of removing a user's hand from a glove comprising:

providing a cuff holding ring holding open a cuff of a glove;

providing a user's hand which is inside the glove;

providing a front plate and a back plate each having a slot;

arranging the front plate and back plate such that they are substantially parallel and such that the slots on each are oriented in the same direction, thereby forming a bracket assembly;

placing the cuff holding ring and the cuff into a space defined between the front plate and the back plate of the bracket assembly for retention thereby;

withdrawing the hand through the cuff holding ring in a direction substantially transverse to the placing motion.

* * * * *